United States Patent [19]

Heine et al.

[11] Patent Number: 4,675,919
[45] Date of Patent: Jun. 30, 1987

[54] HEADBAND WITH CUSHION

[75] Inventors: Helmut A. Heine, Herrsching; Werner Theissig, Munich, both of Fed. Rep. of Germany

[73] Assignees: Proper Manufacturing Co. Inc., Long Island City, N.Y.; Heine Optotechnik GmbH, Herrsching, Fed. Rep. of Germany; a part interest

[21] Appl. No.: 858,347

[22] Filed: May 1, 1986

[30] Foreign Application Priority Data

May 8, 1985 [DE] Fed. Rep. of Germany ....... 3516581

[51] Int. Cl.⁴ ................................................ A42B 1/06
[52] U.S. Cl. .......................................... 2/410; 2/181; 2/181.4
[58] Field of Search .................. 2/410, 411, 414, 422, 2/412, 171, 181, 181.4, DIG. 11

[56] References Cited

U.S. PATENT DOCUMENTS 3,280,406 10/1966 Immel .................................... 2/181
3,495,272 2/1970 Tempelhof ...................... 2/181.4 X
3,906,548 9/1975 Kallis ................................... 2/181.4

Primary Examiner—Werner H. Schroeder
Assistant Examiner—J. L. Olds
Attorney, Agent, or Firm—Amster, Rothstein & Ebenstein

[57] ABSTRACT

A headband for the mounting of devices carried on the head, in particular medical optical instruments, includes removable cushions which are constructed of an elastic material of stable shape and are located on the headband at regions at which it comes into contact with the head of the user. The cushions include strap profiles with edge strips, which extends along the sides of the cushions and which engage the edges of the headband for securing the cushions thereto.

8 Claims, 2 Drawing Figures

HEADBAND WITH CUSHION

The invention relates to a headband for the mounting of devices carried on the head, in particular optical instruments, having at least one removable cushion located at at least one section of the headband.

Headbands capable of carrying devices, such as optical instruments, are principally used by doctors. A simple, generally known headband construction is, for example, the headband with a head mirror. However, simple headbands are only suitable as a mounting for light weight instruments, in which no adjustment is necessary. For larger and heavier instruments and/or for those which require an accurate optical adjustment, such as ophthalmoscopes for the examination of the eyes, a more stable headband with a supplementary band extending over the head is used. With such an arrangement the periphery and the height of the headband are, in general, adjustable.

In order to achieve a comfortable and at the same time secure, non-slip seating of the headband, the regions of the headband which come into contact with the forehead, back of the head and crown of the user are provided with cushions. The simplest cushion consists of strips of foam material, which are cemented to the internal surfaces of the headband. The disadvantage of this arrangement is that the cleaning of the cushion is very difficult and with the passage of time the foam material dissolves under the action of skin grease and sweat. More expensive cushions are those formed of a lined plastic foil material with a smooth external surface and a foam material inlaid or cemented in. These cushions are placed around the appropriate sections of the headband and secured by means of press-studs, slide fasteners or touch-and-close fasteners. This type of cushion is less sensitive to grease and sweat. Disadvantages are costly manufacture and awkward removal and fitting of the cushion to the headband. Over and above this, the non-slip securing of the headband can only be achieved by means of a tight and therefore uncomfortable seating.

The object of the invention is to provide a headband with a cushion which is simple to manufacture, simple to fit and ensures a good seating.

Proceeding from the headband mentioned in the introduction, this object is achieved according to the invention in that the cushion is constructed of an elastic material of stable shape and includes a strap profile, which profile extends over the edges of the headband and engages the headband at the edges.

The headband cushion according to the invention can be produced as a mass production article at low cost, in the form of a foamed moulded part. For fitting to the headband, it is simply pressed onto the appropriate sections of the headband, the strap profile extending over the edges of the headband and engaging thereat, and for removal it is simply pulled off. Nevertheless, a good seating both of the cushion to the headband and also of the headband, including instruments fitted thereto, to the head of the user is achieved by this cushion.

Preferably, the cushion consists of integral foam material based on polyurethane. Such a cushion is very flexible and at the same time is of very stable shape. It exhibits a skin-like, closed-pore surface, and is absolutely resistant to grease and sweat, as well as to all conventional cleansing agents and disinfectants. The closed-pore surface does not absorb any moisture whatsoever. As a result of the free choice of the surface roughness, the gross density and thus the softness as well as the thickness of the cushion, the best possible adaptation to the anatomical features is possible, and a seating of the headband which is both comfortable and also extremely good can be achieved. The cushion adapts itself to differing curvatures of the headband without forming folds.

The strap profile can be constructed substantially over the entire length of the cushion. In this arrangement, the strap profile can be interrupted by recesses, for example, in the region of an adjustment device for the periphery or the height of the headband. Alternatively, the strap profile can also be formed from a number of hooks disposed along the longitudinal sides of the cushion.

The invention will be explained in greater detail with reference to the exemplary embodiments shown in the drawing. In the drawing.

Figure 1:
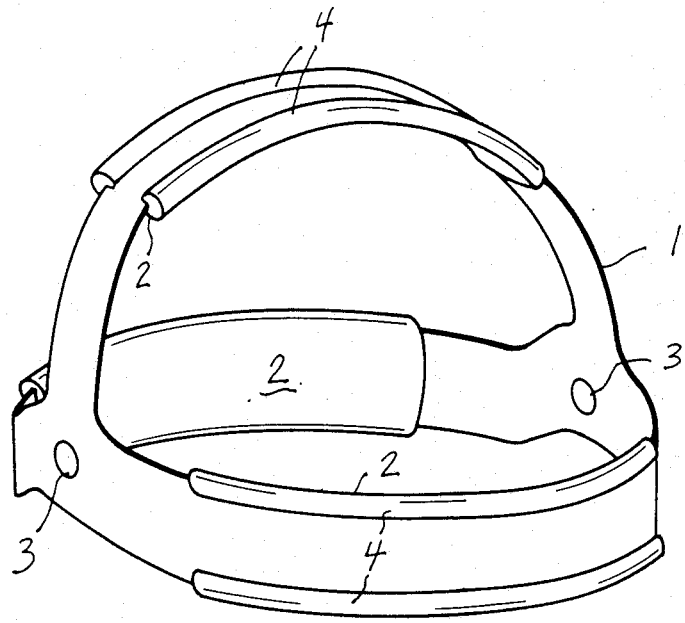
FIG. 1 shows an overall view of a headband.

The headband 1 shown in FIG. 1 is provided with cushions 2 at the regions at which it comes into contact with the forehead, the back of the head and the crown of the user. There can be fitted to the headband 1, e.g. by means of a stirrup (not shown) securable at the points 3, optical instruments for medical examinations, such as binocular indirect ophthalmoscopes or binocular magnifiers and the like. With such an arrangement, an accurate optical adjustment of the instruments is possible by means of the headband. The periphery and height of the headband 1 can be adjusted by devices (also not shown), in order to adapt the headband to the user and to achieve a secure, non-slip seating, even when relatively heavy instruments are used.

Figure 2:
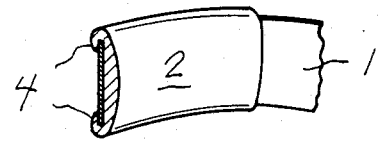
FIG. 2 shows a cross-section through the headband at a cushioned section.

The cushions 2 are produced from soft integral foam material based on polyurethane, and include a strap profile with clips or edge strips 4, which extend along the longitudinal sides of the cushions and which extend over the narrow side edges of the regions of the headband 1 which are to be cushioned, in the manner of hooks or clamps (FIG. 2). On fitting the cushion 2 to the headband 1, the edge strips 4 are pressed over the edges of the headband 1 and then engage the headband on account of the elastic properties of the cushion 2. On account of the stable-shape properties of the cushion 2, the clips 4 reliably secure the cushion 2 to the headband 1, without further additional securing elements. The width of the cushion 2 is selected in accordance with the width of the headband 1. The edge strips 4 or the strap profile can be interrupted in the region of an adjustment device for the periphery and height of the headband 1, in order to permit easy access to this device and simple operation.

In place of edge straps 4 extending over the entire length of the cushion 2 or substantial sections thereof, the strap profile can also consist of individual hooks, which are disposed along the longitudinal sides of the cushion 2 and which extend in the manner of the edge strips 4 over the edge of the headband 1 and effect securing of the cushion 2 thereat, the only difference being that the securing is effected at points and not along lines.

As will be readily apparent to those skilled in the art, the invention may be used in other specific forms or for other purposes without departing from its spirit or central characteristics. The present embodiments are therefore to be considered as illustrative and not restrictive, the scope of the invention being indicated by the claims rather than by the foregoing description, and all embodiments which come within the range of equivalence of the claims are intended to be embraced.

We claim:

1. A headband for the mounting of devices carried on the head, in particular optical instruments, comprising at least one removable cushion of one-piece integral construction located at at least one section of the headband, said cushion being constructed of an elastic material of uniform composition and stable shape and including a strap profile, said profile extending over edges of the headband and engaging the headband at the edges thereof to secure the cushion to the headband.

2. The headband of claim 1, in which the cushion is constructed of integral foam material based on polyurethane.

3. The headband of claim 1 in which the strap profile extends substantially over the entire length of the cushion.

4. The headband of claim 2 in which the strap profile extends substantially over the entire length of the cushion.

5. A removable cushion of one-piece integral construction adapted to be received on at least one section of a headband utilized for the mounting of devices carried on the head, said cushion being constructed of an elastic material of uniform composition and stable shape and including a strap profile, said profile extending over edges of the headband and engaging the headband at the edges thereof to secure the cushion to the headband.

6. The cushion of claim 5, which is constructed of integral foam material based on polyurethane.

7. The cushion of claim 5 in which the strap profile extends substantially over the entire length of the cushion.

8. The cushion of claim 6 in which the strap profile extends substantially over the entire length of the cushion.

* * * * *